(12) United States Patent
Boiangiu

(10) Patent No.: US 9,861,482 B2
(45) Date of Patent: *Jan. 9, 2018

(54) DENTAL BONE IMPLANT AND IMPLANT METHOD

(71) Applicant: Andy Boiangiu, Holon (IL)

(72) Inventor: Andy Boiangiu, Holon (IL)

(*) Notice: Subject to any disclaimer, the term of this patent is extended or adjusted under 35 U.S.C. 154(b) by 40 days.

This patent is subject to a terminal disclaimer.

(21) Appl. No.: 15/044,557

(22) Filed: Feb. 16, 2016

(65) Prior Publication Data

US 2016/0157965 A1 Jun. 9, 2016

Related U.S. Application Data

(63) Continuation-in-part of application No. 13/648,048, filed on Oct. 9, 2012, now Pat. No. 9,259,320, which
(Continued)

(51) Int. Cl.
| | |
|---|---|
| *A61F 2/02* | (2006.01) |
| *A61F 2/28* | (2006.01) |
| *A61C 8/02* | (2006.01) |
| *A61C 1/08* | (2006.01) |
| *A61F 2/30* | (2006.01) |

(52) U.S. Cl.
CPC .......... *A61F 2/2803* (2013.01); *A61C 1/084* (2013.01); *A61C 8/0006* (2013.01); *A61F 2/2846* (2013.01); *A61F 2002/2835* (2013.01); *A61F 2002/30777* (2013.01); *A61F 2002/30784* (2013.01); *A61F 2002/30948* (2013.01)

(58) Field of Classification Search
CPC .............. A61C 8/0006; A61F 2/2803; A61F 2002/2807; A61F 2002/283
See application file for complete search history.

(56) References Cited

U.S. PATENT DOCUMENTS

| | | | |
|---|---|---|---|
| 5,639,850 A | 6/1997 | Bryant | |
| 6,409,764 B1 | 6/2002 | White | |

(Continued)

FOREIGN PATENT DOCUMENTS

| | | |
|---|---|---|
| DE | 102006047054 A1 | 4/2008 |
| WO | 2010099333 A2 | 9/2010 |

OTHER PUBLICATIONS

International Search Report for parent PCT application PCT/IL2009/000826, issued by European Patent Office dated May 3, 2010.
(Continued)

*Primary Examiner* — Brian Dukert
(74) *Attorney, Agent, or Firm* — Simon Kahn; Chanoch Kahn

(57) ABSTRACT

A dental bone implant constituted of: a superstructure sized and shaped to fit tightly to a periodontal alveolar bone, the superstructure constituted of: a first face arranged to face a surface of the periodontal alveolar bone; a second face, opposing the first face; and a plurality of perforations extending from the first face to the second face, and non-solidified bone augmentation material deposited within the plurality of perforations, wherein the perforations are of a size sufficient to secure the non-solidified bone augmentation material deposited within the plurality of perforations.

18 Claims, 8 Drawing Sheets

Related U.S. Application Data is a continuation-in-part of application No. 13/060,449, filed as application No. PCT/IL2009/000826 on Aug. 26, 2009, now Pat. No. 8,398,714.

(60) Provisional application No. 61/136,299, filed on Aug. 26, 2008, provisional application No. 61/545,160, filed on Oct. 9, 2011.

(56) References Cited

U.S. PATENT DOCUMENTS

| | | | |
|---|---|---|---|
| 6,686,437 B2 | 2/2004 | Buchman et al. | |
| 7,771,482 B1 | 8/2010 | Karmon | |
| 7,799,754 B2 | 9/2010 | Hart et al. | |
| 7,943,573 B2 | 5/2011 | Lynch et al. | |
| 8,485,820 B1* | 7/2013 | Ali | A61C 8/0027 433/173 |
| 2002/0110785 A1 | 8/2002 | Ashman | |
| 2004/0024466 A1 | 2/2004 | Heerklotz et al. | |
| 2004/0044413 A1 | 3/2004 | Schulter | |
| 2004/0054415 A1 | 3/2004 | Schulter | |
| 2005/0159754 A1 | 7/2005 | Odrich | |
| 2005/0209595 A1 | 9/2005 | Karmon | |
| 2008/0228279 A1 | 9/2008 | Hall | |
| 2010/0255053 A1 | 10/2010 | Savage - Erickson | |
| 2010/0255446 A1 | 10/2010 | Better et al. | |
| 2010/0291508 A1 | 11/2010 | Jensen | |
| 2011/0035024 A1 | 2/2011 | Malmquist et al. | |
| 2012/0129133 A1 | 5/2012 | Kaigler, Sr. | |
| 2012/0148984 A1 | 6/2012 | Kaigler, Sr. | |
| 2017/0028104 A1* | 2/2017 | Meretzki | A61K 31/728 |

OTHER PUBLICATIONS

McAllister et al., "Bone Augmentation Techniques", Journal of Periodontology, vol. 78, No. 3, Mar. 2007, pp. 377-396.

Fukuda et al., "Bone Ingrowth into Pores of Lotus Stem-Type Bioactive Titanium Implants Fabricated Using Rapid Prototyping Technique", Journal of the International Society for Ceramics in Medicine, 2011, vol. 1, pp. 1-3.

* cited by examiner

| 2000 | PROVIDE SUPERSTRUCTURE SHAPED AND SIZED TO FIT TIGHTLY OVER A PERIODONTAL ALVEOLAR BONE AND COMPRISING: FIRST AND SECOND OPPOSING FACES; AND A PLURALITY OF PERFORATIONS EXTENDING FROM FIRST TO SECOND FACE, OPTIONALLY EXHIBITING WIDTH OF 500 – 1200 UM |
|---|---|
| 2010 | DEPOSIT NON-SOLIDIFIED BONE AUGMENTATION MATERIAL WITHIN PERFORATIONS, OPT. AUTOLOGOUS, OPT. FORMED FROM STEM CELLS DERIVED FROM ADIPOSE TISSUE, OPT. COMPRISING BONE CELLS AND ENDOTHELIAL CELLS, OPTIONALLY GROWN ON A 3D MINERAL SCAFFOLD OR MATRIX |
| 2020 | FIT SUPERSTRUCTURE OVER PERIODONTAL ALVEOLAR BONE |

FIG. 8

DENTAL BONE IMPLANT AND IMPLANT METHOD

CROSS-REFERENCE TO RELATED APPLICATIONS

This application claims priority from U.S. Provisional Application 61/545,160 filed Oct. 9, 2011 and is a continuation-in-part of U.S. patent application Ser. No. 13/648,048 filed Oct. 9, 2012, which is a continuation-in-part of U.S. patent application Ser. No. 13/060,449 which is a National Phase application of PCT/IL2009/000826 with International Filing Date Aug. 26, 2009, and which PCT/IL2009/000826 claims priority from U.S. Provisional Application 61/136,299 filed Aug. 26, 2008.

TECHNICAL FIELD

The present invention relates generally to the field of bone augmentation and in particular to an apparatus comprising a superstructure with perforations arranged to secure bone augmentation material therein.

BACKGROUND

Bone loss in the jaw can occur for a number of reasons, including but not limited to: periodontal disease causing an inflammation, thereby destroying periodontal structure and bone; atrophy of the jaw bone because of a missing tooth, or teeth, such that the bone becomes inactive at the point of the missing tooth; and damage caused by an external source. If it is desired to attach a medical implant to the jaw, such as a dental implant for a missing tooth, a sufficient amount of bone must be present in order for the implant to be properly attached to the bone. However, if bone loss has occurred there may not be a sufficient amount of bone.

Bone augmentation is a process of causing the bone to regenerate, thereby increasing the amount of bone in the area destined for the medical implant. Vertical bone augmentation is a process where a structure is attached to a bone surface of an area exhibiting a bone defect, i.e. bone loss, the structure extending outward from the bone surface. Bone augmentation material is then disposed within the structure thereby allowing the defected bone to grow. Vertical bone augmentation is used in cases where the bone loss is such that no structure exists in the remaining bone for placement of the bone augmentation material.

Various techniques have been developed to serve as containers for vertical bone augmentation, with limited success. U.S. Pat. No. 7,771,482 issued Aug. 10, 2010 to Karmon is addressed to bioresorbable inflatable devices, a tunnel incision tool and methods for treating and enlarging a tissue or an organ or a tube or a vessel or a cavity. The device is composed of a hollow expanding pouch made of a resorbable material that can be attached to a filling element. Unfortunately, such hollow expanding pouch is not ideally suited for use with oral bone augmentation, where excessive mechanical pressures on the pouch may be experienced.

Thus, there is a long felt need for a structure arranged to have improved bone augmentation material disposed therein to provide for vertical bone augmentation, the structure exhibiting properties superior to the structures of the prior art.

SUMMARY

Accordingly, it is a principal object to overcome at least some of the disadvantages of prior art. This is accomplished in certain embodiments by providing a dental bone implant comprising: a superstructure sized and shaped to fit tightly to a periodontal alveolar bone, the superstructure comprising: a first face arranged to face a surface of the periodontal alveolar bone; a second face, opposing the first face; and a plurality of perforations extending from the first face to the second face, and non-solidified bone augmentation material deposited within the plurality of perforations, wherein the perforations are of a size sufficient to secure the non-solidified bone augmentation material deposited within the plurality of perforations.

Additional features and advantages will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 8 illustrates a high level flow chart of a method of implanting a dental implant, according to certain embodiments.

DETAILED DESCRIPTION OF THE PREFERRED EMBODIMENTS

Figure 1A:
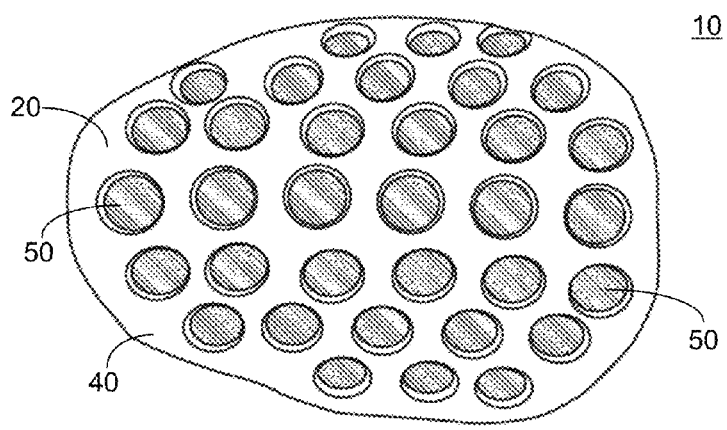
FIGS. 1A-1C illustrate a plurality of high level views of an exemplary apparatus for bone augmentation comprising a superstructure which comprises a plurality of perforations each exhibiting a generally circular width, according to certain embodiments.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
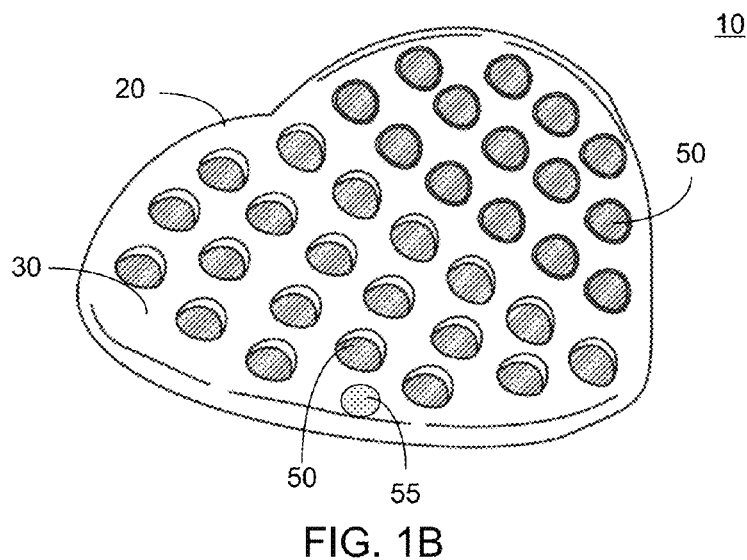
Figure 1C:
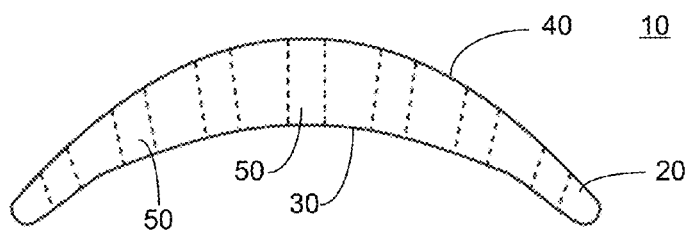

FIG. 1A illustrates a high level top view of an exemplary bone augmentation apparatus 10, FIG. 1B illustrates a high level bottom view of bone augmentation apparatus 10 and FIG. 1C illustrates a high level side cut view of bone augmentation apparatus 10, the figures being described together. Bone augmentation apparatus 10 comprises: a superstructure 20, exhibiting a first face 30; a second face 40, opposing first face 30; and a plurality of perforations 50, each extending from first face 30 to second face 40. Surgical guide 55 is further optionally provided, as will be described further below. Superstructure 20 comprises a biocompatible material having a strength and tensility sufficient to be permanently stationed between an upper jaw and a lower jaw. In one embodiment, superstructure 20 is essentially constituted of the biocompatible material.

In one embodiment, the biocompatible material comprises titanium. In another embodiment, the biocompatible material comprises a polyimide. In one further embodiment, the polyimide is not bioreplaceable, i.e. is not absorbed in bone or tissue. In one further embodiment, the tensile strength of the polyimide is 80-140 MPa, preferably 90-130 MPa. In one embodiment, the tensile modulus of the polyimide is 2,900-4,600 MPa, preferably 3,300-4,200 MPa. Advantageously, the above described tensile strength and modulus of the polyimide prevents disintegration and/or crumbling responsive to bone growth thereon and to resist the mechanical forces experienced in the oral environment. In one embodiment, the polyimide comprises MP-1 polyimide. In one embodiment, the porosity of the polyimide is 1.4-2.2 percent, preferably 1.6-2 percent. Superstructure 20 is illustrated as being saddle shaped, however this is not meant to be limiting in any way and superstructure 20 is configured and dimensioned so as to properly ameliorate a particular bone defect as will be described below.

In one embodiment, each perforation 50 exhibits a width of 500-1200 um. In one particular embodiment, each perforation 50 exhibits a width of about 500 um. In another particular embodiment, each perforation 50 exhibits a width of about 600 um. In another particular embodiment, each perforation 50 exhibits a width of about 900 um. In another particular embodiment, each perforation 50 exhibits a width of about 1200 um. In one embodiment, plurality of perforations 50 exhibit widths of different dimensions are provided, the dimensions being determined according to desired performance. Specifically, as will be described below, in operation bone grows through perforations 50, and perforations 50 function as containers for bone augmentation material. Perforations 50 exhibiting a larger width offer improved bone growth at early stages of the growth process, thus not interfering with normal growth patterns, however too large a width may result in improper containment of the bone augmentation material. Perforations 50 exhibiting a smaller width offer improved bone growth over longer periods of time while inhibiting growth at the early stages, and may offer improved containment of the bone augmentation material. Thus, perforations 50 exhibiting widths of different sizes are preferred. In one non-limiting embodiment, perforations 50 are constructed with any of: computer numerical controlled (CNC) milling; or laser cutting. In one non-limiting embodiment, superstructure 20 is generated by 3 dimensional printing, advantageously allowing for rapid production thereby reducing the waiting period from measurement of the necessary dimensions and configuration of superstructure 20 until disposing thereof within a bone defect, as will be described below. Perforations 50 are illustrated each exhibiting a generally circular width, however this is not meant to be limiting in any way and perforations 50 may be provided exhibiting widths of a plurality of configurations without exceeding the scope. For the sake of clarity, perforations 50 are each illustrated with a background to emphasize the depth thereof.

Bone augmentation apparatus 10 may further comprise one or more surgical guides 55, as described in PCT application PCT/IL2009/000826, published as WO2010/023665 A2, the entire contents of which is incorporated herein by reference. Surgical guide markings, recesses, extensions and/or bores which are indicative of one or more drilling locations and/or dental implant locations for use when bone augmentation apparatus 10 is placed on the treated area, are specifically contemplated.

Figure 2:
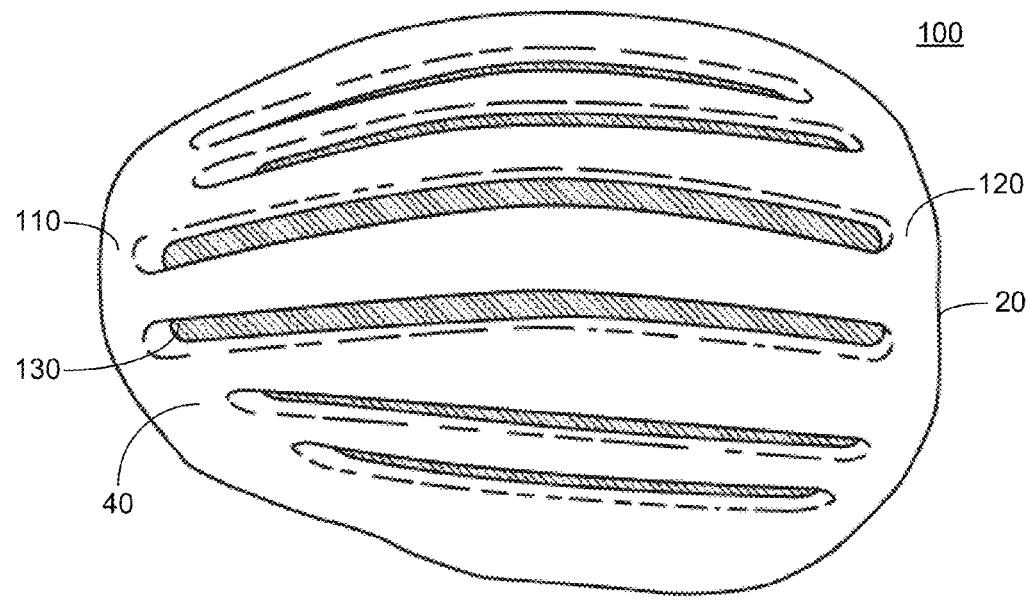
FIG. 2 illustrates a high level view of an exemplary apparatus for bone augmentation comprising a superstructure which comprises a plurality of elongate perforations.

FIG. 2 illustrates a high level top view of a bone augmentation apparatus 100 comprising a superstructure 20, exhibiting: a first face 30 (not shown); a second face 40, opposing first face 30; a first end 110; a second end 120, opposing first end 110; and a plurality of elongate perforations 130 extending from first face 30 to second face 40. Each elongate perforation 130 extends from first end 110 to second end 120 along the entire length thereof. As described above in relation to perforations 50 of bone augmentation apparatus 10, in one embodiment each elongate perforation 130 exhibits a width of 500-1200 um. In one particular embodiment, each elongate perforation 130 exhibits a width of about 500 um. In another particular embodiment, each elongate perforation 130 exhibits a width of about 600 um. In another particular embodiment, each elongate perforation 130 exhibits a width of about 900 um. In another particular embodiment, each elongate perforation 130 exhibits a width of about 1200 um. In one embodiment, plurality of elongate perforations 130 exhibit widths of different dimensions are provided, the dimensions being determined according to desired performance. For the sake of clarity, perforations 130 are each illustrated with a background to emphasize the depth thereof.

Bone augmentation apparatus 100 may further comprise one or more surgical guides, as described in PCT application PCT/IL2009/000826, published as WO2010/023665 A2, the entire contents of which is incorporated herein by reference. Surgical guide markings, recesses, extensions and/or bores which are indicative of one or more drilling locations and/or dental implant locations for use when bone augmentation apparatus 10 is placed on the treated area, are specifically contemplated.

Figure 3:
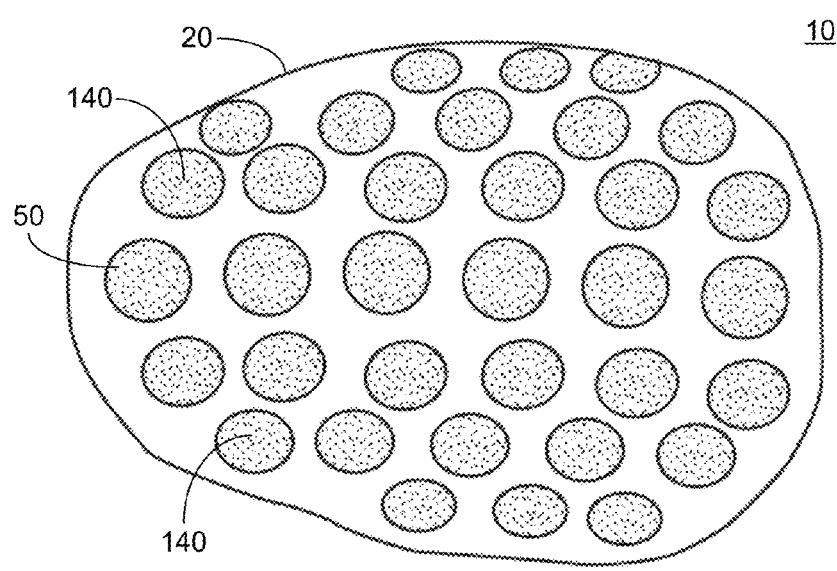
FIG. 3 illustrates a high level view of the apparatus of FIGS. 1A-1C further comprising bone augmentation material deposited within the plurality of perforations.

FIG. 3 illustrates a high level top view of bone augmentation apparatus 10 of FIGS. 1A-1C further comprising bone augmentation material 140 deposited within perforations 50, as will be described below.

Figure 4A:
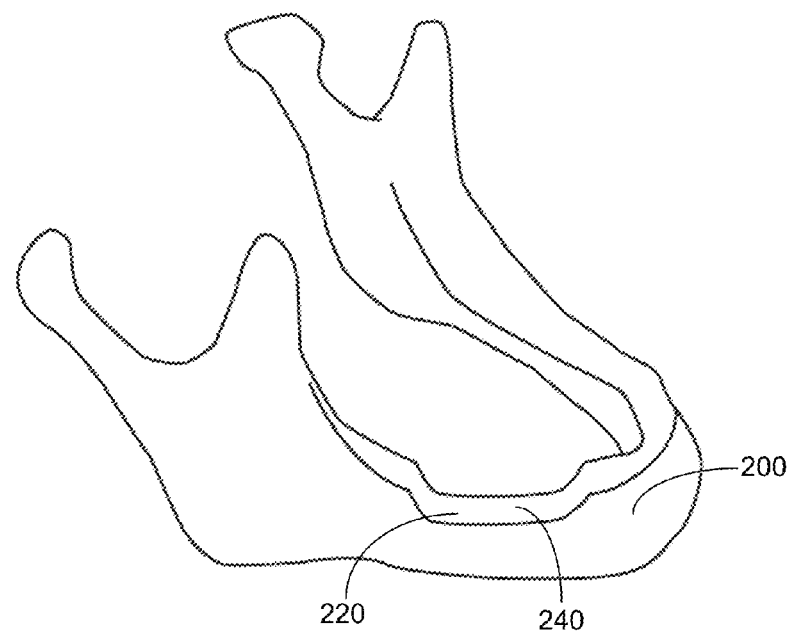
FIG. 4A illustrates a jaw exhibiting an area with a bone defect.

FIG. 4A illustrates a jaw 200 exhibiting a bone defect 220. Bone defect 220 may be any of: dehiscences or fenestrations of the alveolar crest and/or bone; horizontal bone defects; vertical bone defects; burr like holes; and holes and fractures caused by a periodontal disease.

In order to prepare an appropriate bone augmentation apparatus 10 or 100, the mandible and/or the maxilla of the patient, or any portion thereof, is imaged, such as jaw 200. For brevity, the mandible, the maxilla, and/or any portion thereof may be referred to herein, separately or jointly, as jaw 200 of the patient. Such imaging data optionally includes a three dimensional (3D) representation of jaw 200. The imaging data is captured by a device capable of capturing an intra-oral image of the mouth of a patient, in one embodiment being any of: a 3D modality, such as a micro laser optical device, a computerized tomography (CT) modality, an intra-oral camera, and an ultrasound modality; a magnetic resonance imager (MRI) modality; an MRI-CT (MRT) modality; a cone beam CT (CBCT) modality; and a confocal scanning modality. Optionally, the imaging data is acquired from a medical imaging database, such as a picture archiving and communication system (PACS).

A superstructure 20, such as superstructure 20 of apparatus 10 or apparatus 100 is produced, the configuration thereof responsive to the received intra-oral image of jaw 200. Particularly, the configuration and dimension of superstructure 20 is determined to substantially ameliorate bone defect 220 when disposed therein. Advantageously, as described above, superstructure 20 is in one embodiment produced by any of: CNC milling; laser cutting; and 3 dimensional printing. These methods allow for rapid production of superstructure 20 thereby the waiting period from the time of imaging until the time of disposing thereof within bone defect 220 is significantly reduced.

Figure 4B:
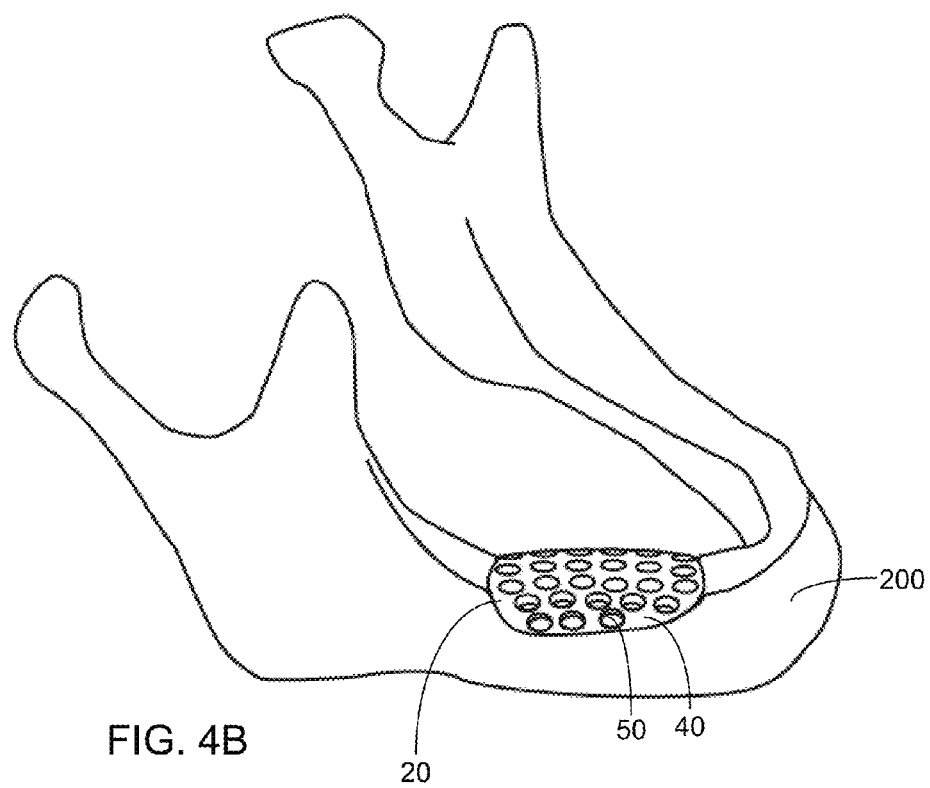
FIG. 4B illustrates a high level view of the apparatus of FIGS. 1A-1C disposed within the bone defect of the jaw of FIG. 4A.

A bone surface 240 of bone defect 220 is surgically exposed. As illustrated in FIG. 4B, superstructure 20 is disposed within bone defect 220 such that first face 30 (not shown) is facing, and preferably in contact with, bone surface 240 of bone defect 220. Superstructure 20 is secured to jaw 200 by an adhesive material and/or one or more screws.

Bone augmentation material 140 (not shown) is deposited within perforations 50 of superstructure 20, as illustrated above in relation to FIG. 3. In one embodiment, bone augmentation material 140 is bioreplaceable. In one embodiment, bone augmentation material 140 comprises bone morphogenetic proteins (BMPs) know to induce the formation of bone and cartilages. In another embodiment, bone augmentation material 140 comprises any of: transforming growth factor (TGF)-PI; insulin growth factor (IGF); fibroblast growth factor FGF; platelet derived growth factor (PDGF) and epidermal growth factor EGF; ions such as strontium and/or mixed with bone marrow which aspirate to increase biological activity; human growth factors; and Morphogens, such as bone morphogenic proteins in conjunction with a carrier medium, such as collagen. In one embodiment, bone augmentation material 140 comprises bone granules.

In one embodiment, first face 30 of superstructure 20 is at least partially coated with bone augmentation material 140. In one embodiment, the coating is carried out during production of superstructure 20. In another embodiment, the coating is carried out just prior to disposing of superstructure 20 within bone defect 220. In one embodiment, second face 40 of superstructure 20 is at least partially coated with bone augmentation material 140. In one embodiment, the coating is carried out during production of superstructure 20. In another embodiment, the coating is carried out just prior to disposing of superstructure 20 within bone defect 220 and in another embodiment the coating is carried out subsequent to disposing of superstructure 20 within bone defect 220. In one embodiment, bone augmentation material 140 is deposited within perforations 50 during production of superstructure 20.

Bone augmentation material 140 deposited within perforations 50 and optionally coated over first face 30 causes bone defect 220 to begin to regenerate and grow. Advantageously, plurality of perforations 50 allow bone to grow through superstructure 20 and superstructure 20 remains as a support structure during bone growth. In the embodiment where second face 40 is at least partially coated with bone augmentation material 140, bone growth is additionally aided after the bone grows out of perforations 50 and over second face 40 of superstructure 20. As described above, in one embodiment superstructure 20 comprises a biocompatible non-bioreplaceable material thereby superstructure 20 remains as a support structure during all stages of bone growth and thereafter. As described above, superstructure 20 comprises a material exhibiting a strength and tensility sufficient to withstand the pressure of bone growth and to resist the mechanical forces experienced in the oral environment. Advantageously, biocompatible properties of superstructure 20 allow superstructure 20 to remain in place even after bone growth is completed and subsequent surgery to remove superstructure 20 is not necessary.

Figure 5:
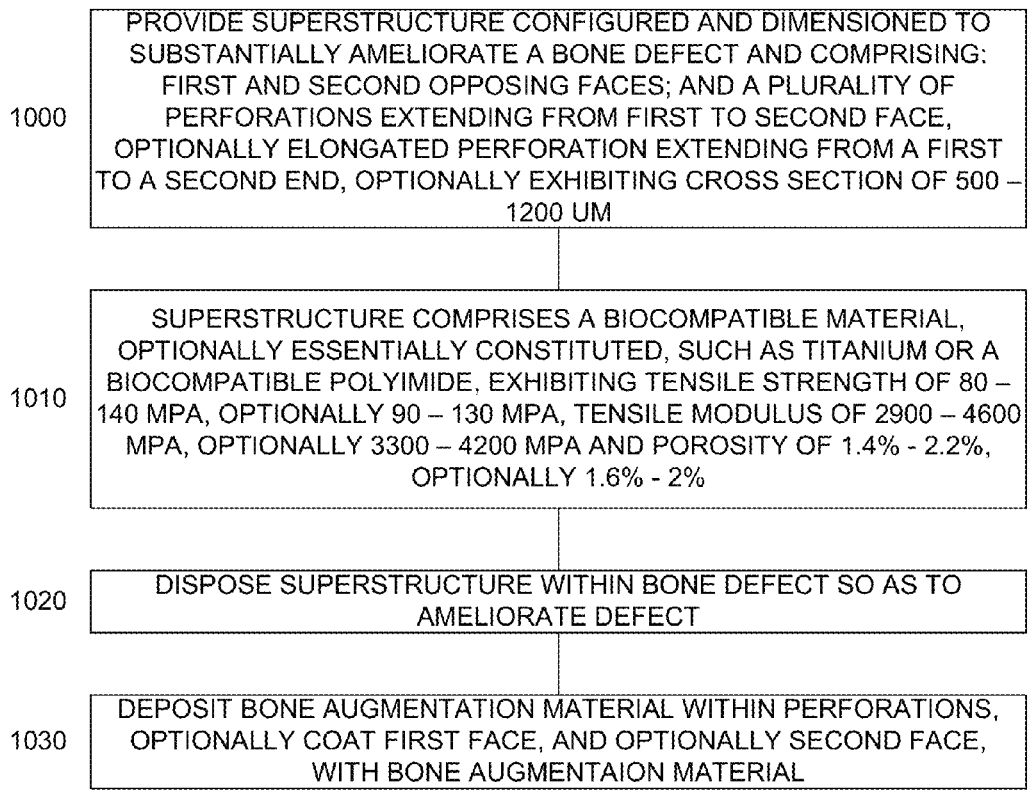
FIG. 5 illustrates a high level flow chart of a first method of bone augmentation, according to certain embodiments.

FIG. 5 illustrates a high level flow chart of a first method of bone augmentation, according to certain embodiments. In stage 1000, a superstructure is provided, the provided superstructure configured and dimensioned to substantially ameliorated a bone defect. The superstructure comprises: a first face arranged to face a bone surface of the bone defect; a second face, opposing the first face; and a plurality of perforations extending from the first face to the second face, the perforations of a size sufficient to secure bone augmentation material deposited within the plurality of perforations. In one embodiment, each of the plurality of perforations exhibits a width of 500-1200 um. In one embodiment, the plurality of perforations exhibit widths of different dimensions. In one embodiment, the provided superstructure further exhibits a first end and a second end, each of the perforations comprising an elongated perforation extending from the first end to the second end.

In stage 1010, the provided superstructure of stage 1000 comprises a biocompatible material having a strength and tensility sufficient to be permanently stationed between an upper and a lower jaw, i.e. strong enough to resist the mechanical forces experienced in an oral environment. In one embodiment, the provided superstructure is essentially constituted of the biocompatible material. In one further embodiment, the biocompatible material comprises titanium. In another further embodiment, the biocompatible material comprises a biocompatible polyimide. In one embodiment, the polyimide is not bioreplaceable, i.e. is not absorbed in bone or tissue. In one embodiment, the tensile strength of the polyimide is 80-140 MPa, preferably 90-130 MPa. In one embodiment, the tensile modulus of the polyimide is 2,900-4,600 MPa, preferably 3,300-4,200 MPa. Advantageously, the above described tensile strength and modulus of the polyimide prevents disintegration and/or crumbling responsive to bone growth thereon and responsive to mechanical forces experienced in the oral environment. In one embodiment, the polyimide comprises MP-1 polyimide. In one embodiment, the porosity of the polyimide is 1.4-2.2 percent, preferably 1.6-2 percent.

In stage 1020, the provided superstructure of stage 1000 and stage 1010 is disposed within the bone defect so as to substantially ameliorate the bone defect. In one embodiment, the superstructure is secured in place by an adhesive material and/or screws. In stage 1030, bone augmentation material is deposited within the plurality of perforations of the provided superstructure of stage 1000 and 1010. In one embodiment, the first face of the superstructure is at least partially coated with bone augmentation material. In one embodiment, the second face of the superstructure is at least partially coated with bone augmentation material.

Advantageously, the above methods provide a shaped to fit augmentation apparatus. Such a shaped to fit apparatus is particularly advantageous following implantitis, and in particular peri-implantitis, where the resultant bone condition may be non-uniform, at least partially as a result of bone resorption.

Figure 6A:
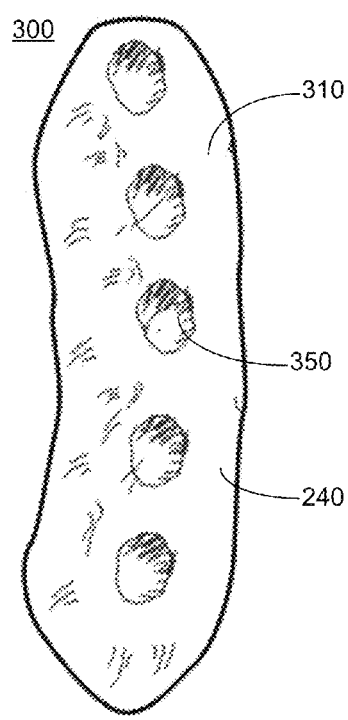
FIG. 6A illustrates a portion of an alveolar bone.
Figure 6B:
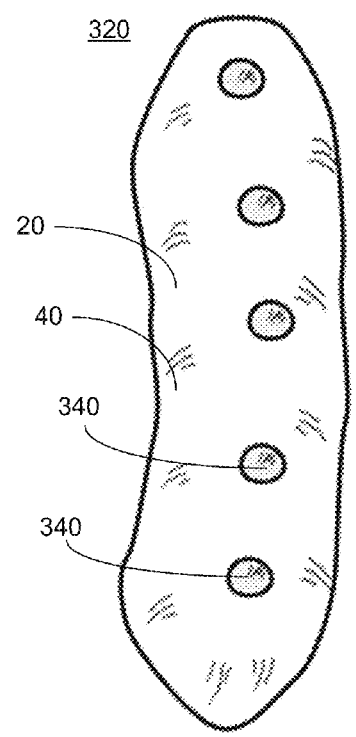
FIG. 6B illustrates a bone graft arranged to be positioned on the alveolar bone portion of FIG. 6A, according to certain embodiments.
Figure 6C:
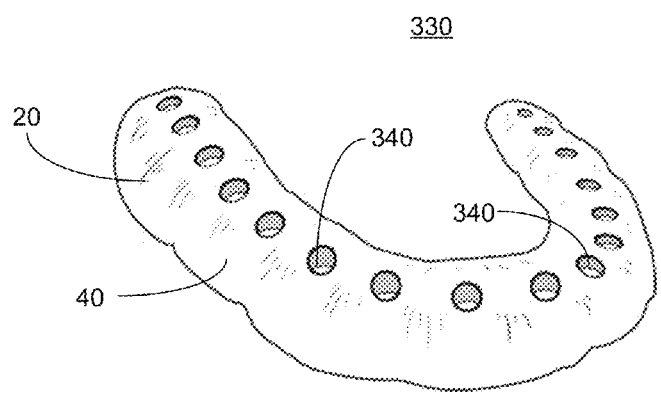
FIG. 6C illustrates a bone graft arranged to be positioned on an alveolar bone, according to certain embodiments.
Figure 6D:
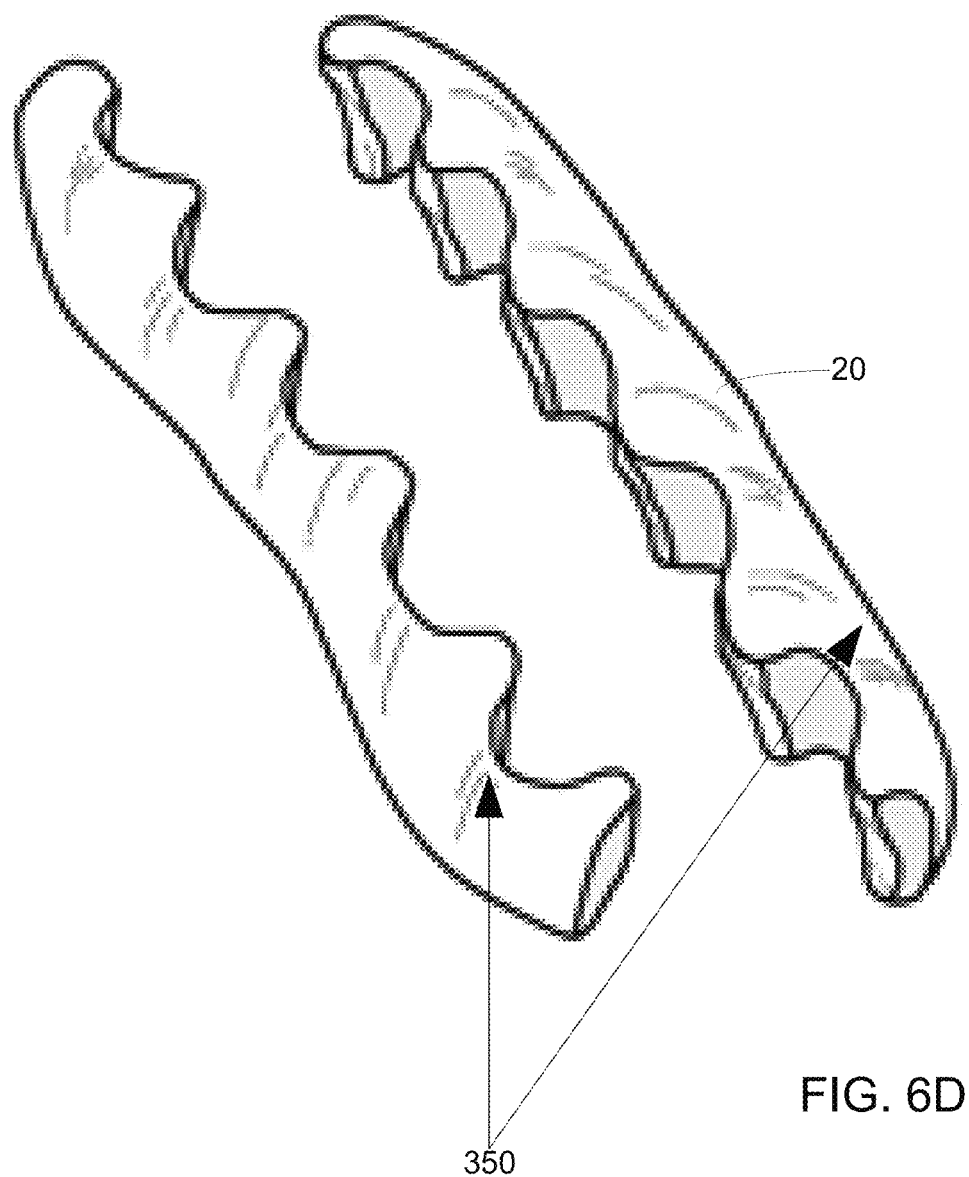
FIG. 6D illustrates a pair of bone grafts arranged to be positioned on either sides of an alveolar bone, according to certain embodiments.

FIG. 6A illustrates a portion 300 of an alveolar bone 310; FIG. 6B illustrates a bone graft 320 arranged to be positioned over alveolar bone 310 portion 300; FIG. 6C illustrates a bone graft 330 arranged to be positioned over a full alveolar bone surface; and FIG. 6D illustrates a pair of complementary bone grafts 350 arranged to be positioned over alveolar bone 310 portion 300, the FIGS. 6A-6D being described together. The term alveolar bone is defined for the purposes of this document as the portion of either the upper or lower jaw which contains tooth sockets. In one embodiment, bone grafts 320, 330 and 350 in all respects similar to bone augmentation apparatus 10 of FIGS. 1A-1C, with the exception that a plurality of surgical guide holes 340 are provided, as described above in relation to optional surgical guides 55. Each surgical guide hole 340 extends from a first face 40 of a superstructure 20 to a second face 30 of superstructure 20 (not shown). Each surgical guide hole 340 is sized and shaped to receive a tooth structure implant. A plurality of surgical guide holes 340 are illustrated, however this is not meant to be limiting in any way and a single surgical guide hole 340 may be provided without exceeding the scope. Superstructure 20 of bone graft 320 is sized and shaped such that it is arranged to be positioned over portion 300 of alveolar bone 310. Superstructure 20 of bone graft 330 is sized and shaped such that it is arranged to be positioned over alveolar bone 310 and extend along the entirety of alveolar bone 310. Superstructure 20 of each bone graft 350 is sized and shaped such that it is arranged to be positioned over a respective one of a buccal and lingual surface of alveolar bone 310. As described above in relation to bone augmentation apparatus 10, a plurality of perforations 50 are provided (not shown) arranged to secure bone augmentation material deposited therein.

In another embodiment, as will be described below in relation to FIGS. 7A-7C, the structure of bone grafts 320, 330 and 350 exhibit a lattice formation.

As described above in relation to bone augmentation apparatus 10, superstructure 20 comprises a biocompatible material. As described above, in one embodiment the biocompatible material comprises titanium. In another embodiment, the biocompatible material comprises a polyimide. In one further embodiment, the polyimide is not bioreplaceable, i.e. is not absorbed in bone or tissue. In one further embodiment, the tensile strength of the polyimide is 80-140 MPa, preferably 90-130 MPa. In one embodiment, the tensile modulus of the polyimide is 2,900-4,600 MPa, preferably 3,300-4,200 MPa. Advantageously, the above described tensile strength and modulus of the polyimide prevents disintegration and/or crumbling responsive to bone growth thereon and to resist the mechanical forces experienced in the oral environment. In one embodiment, the polyimide comprises MP-1 polyimide. In one embodiment, the porosity of the polyimide is 1.4-2.2 percent, preferably 1.6-2 percent.

In operation, as described above superstructure 20 is positioned over alveolar bone 310 such that surface 30 is in contact with bone surface 240. In one embodiment, superstructure 20 is positioned such that each surgical guide hole 340 is positioned over an empty tooth socket of alveolar bone 310. After positioning of superstructure 20, a surgeon drills a hole through each surgical guide hole 340 and a tooth structure implant is inserted through each surgical guide hole 340 into the respective drilled hole. In one embodiment, positioning of superstructure 20 and insertion of tooth structure implants are performed during the same treatment session. Advantageously, the inserted tooth structure implants aid in securing superstructure 20 to bone surface 240. Further advantageously, superstructure 20 aids in securing the inserted tooth structure implants.

Figure 7A:
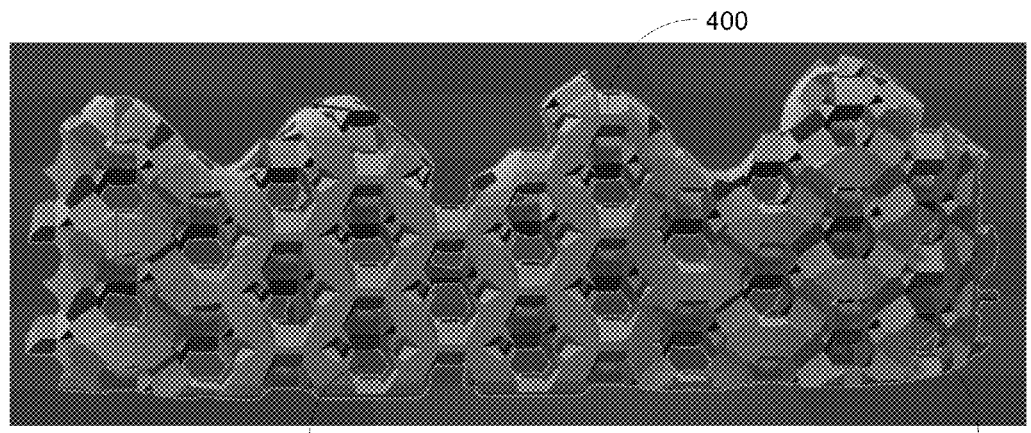
FIGS. 7A-7C illustrate various high level views of a portion of a superstructure of a dental implant, according to certain embodiments.
Figure 7B:
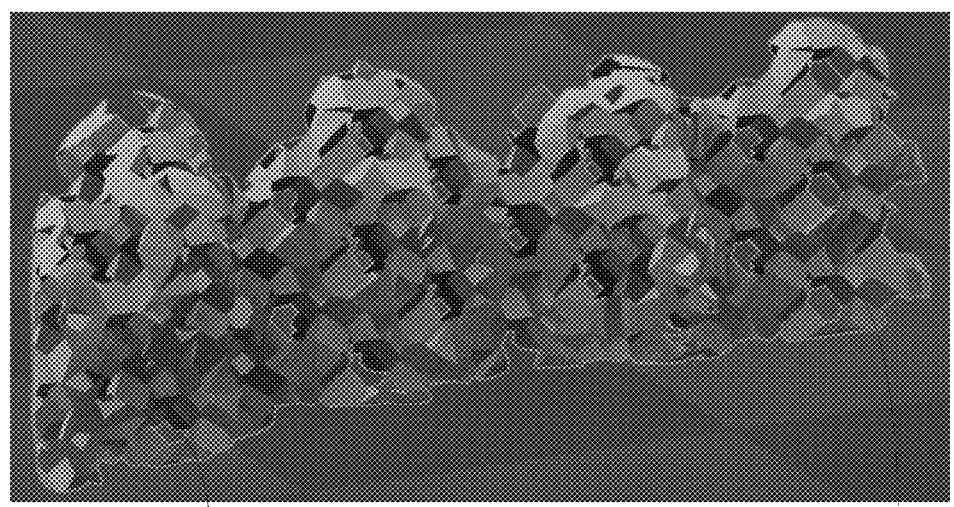
Figure 7C:
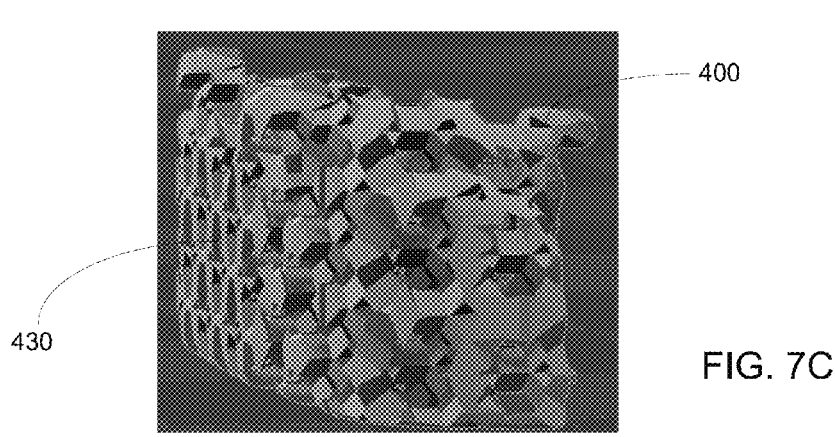

FIGS. 7A-7C illustrate a plurality of high level perspective views of a portion of a superstructure 400 exhibiting a first face 410, a second face 420 and a plurality of perforations 430 extending from first face 410 to second face 420. Perforations 430 give superstructure 400 a lattice structure. Superstructure 400 is composes of a bio-compatible material, as described above. A non-solidified bone augmentation material (not shown) is deposited into perforations 430. In one embodiment, the non-solidified bone augmentation material is a gel, i.e. a non-fluid colloidal network or polymer network that is expanded throughout its whole volume by a fluid. The lattice formation of superstructure 400, with the non-solidified bone augmentation material deposited therein, provides a trabecular bone graft which provides an improved foundation for tooth implants.

In one embodiment, the non-solidified bone augmentation material is autologous. In one embodiment, the autologous bone augmentation material is formed from stem cells derived from adipose tissue. In another embodiment, the autologous bone augmentation material comprises both bone cells and endothelial cells.

In one embodiment, the autologous bone augmentation material further comprises a mineral scaffold or matrix. Particularly, in one embodiment, the stem cells from the patient are seeded on a 3 dimensional (3D) scaffold or matrix where the bone augmentation material is formed. Such a bone augmentation material is commercially available from Bonus BioGroup of Haifa, Israel.

Advantageously, autologous bone augmentation material eliminates the risk of tissue rejection thereby improving the bone augmentation process.

FIG. 8 illustrates a high level flow chart of a second method of bone augmentation, according to certain embodiments. In stage 2000, a superstructure is provided, the provided superstructure sized and shaped to fit tightly to a periodontal alveolar bone. The superstructure comprises: a first face arranged to face a bone surface of the bone defect; a second face, opposing the first face; and a plurality of perforations extending from the first face to the second face, the perforations of a size sufficient to secure bone augmentation material which is deposited within the plurality of perforations. In one embodiment, each of the plurality of perforations exhibits a width of 500-1200 um. In one embodiment, the plurality of perforations exhibit widths of different dimensions. In another embodiment, the plurality of perforations form a lattice formation in the superstructure.

In one embodiment, the first face of the superstructure is at least partially coated with bone augmentation material. In another embodiment, the second face of the superstructure is at least partially coated with bone augmentation material.

In stage 2010, non-solidified bone augmentation material is deposited within the plurality of perforations of stage 2000. In one embodiment, the non-solidified bone augmentation material is in a gel form. In another embodiment, the non-solidified bone augmentation material is autologous. In one further embodiment, the autologous bone augmentation material is formed from stem cells derived from adipose tissue. In another further embodiment, the autologous bone augmentation material comprises bone cells and endothelial cells. In one further embodiment, the autologous bone augmentation material comprises a mineral scaffold or matrix.

In stage 2020, the provided superstructure of stage 2000 is fitted over a periodontal alveolar bone.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. In the claims of this application and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting. No admission is made that any reference constitutes prior art. The discussion of the reference states what their author's assert, and the applicants reserve the right to challenge the accuracy and pertinency of the cited documents. It will be clearly understood that, although a number of prior art complications are referred to herein, this reference does not constitute an admission that any of these documents forms part of the common general knowledge in the art in any country.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A dental bone implant comprising:
    a superstructure sized and shaped to fit tightly to a periodontal alveolar bone, said superstructure comprising:
        a first face arranged to face a surface of the periodontal alveolar bone;
        a second face, opposing said first face; and
        a plurality of perforations independently extending from said first face to said second face without meeting, said plurality of perforations comprising first perforations of a first width and second perforations of a second width, said second width smaller than said first width; and
    non-solidified bone augmentation material deposited within said plurality of perforations,
    wherein said first perforations and said second perforation are each of a size sufficient to secure said non-solidified bone augmentation material deposited within said plurality of perforations.

2. The implant of claim 1, wherein said non-solidified bone augmentation material is in a gel form.

3. The implant of claim 1, wherein said non-solidified bone augmentation material is autologous.

4. The implant of claim 3, wherein said autologous bone augmentation material is formed from stem cells derived from adipose tissue.

5. The implant of claim 4, wherein said autologous bone augmentation material comprises bone cells and endothelial cells.

6. The implant of claim 4, wherein said autologous bone augmentation material further comprises a mineral scaffold or matrix.

7. The implant of claim 1, wherein each of said first perforations and said second perforations exhibits a width of 500-1200 um.

8. The implant of claim 1, wherein one of said first face of said superstructure and said second face of said superstructure is at least partially coated with said non-solidified bone augmentation material.

9. The implant of claim 1, wherein said superstructure further comprises at least one guide hole extending from said first face to said second face, said at least one guide hole sized and shaped to receive a tooth structure implant.

10. A dental bone implanting method, the method comprising:
    providing a superstructure sized and shaped to fit tightly to a periodontal alveolar bone, said provided superstructure comprising:
        a first face arranged to face a surface of the periodontal alveolar bone;
        a second face, opposing said first face; and
        a plurality of perforations each independently extending from said first face to said second face without meeting, said plurality of perforations comprising first perforations of a first width and second perforations of a second width, said second width smaller than said first width,
    depositing non-solidified bone augmentation material within said plurality of perforations,
    wherein said first perforations and said second perforations are each of a size sufficient to secure said non-solidified bone augmentation material deposited within said plurality of perforations; and
    fitting said provided superstructure over the periodontal alveolar bone.

11. The method of claim 10, wherein said deposited non-solidified bone augmentation material is in a gel form.

12. The method of claim 10, wherein said non-solidified bone augmentation material is autologous.

13. The method of claim 12, wherein said autologous bone augmentation material is formed from stem cells derived from adipose tissue.

14. The method of claim 13, wherein said autologous bone augmentation material comprises bone cells and endothelial cells.

15. The method of claim 13, wherein said autologous bone augmentation material further comprises a mineral scaffold or matrix.

16. The method of claim 10, wherein each of said first perforations and said second perforations exhibits a width of 500-1200 um.

17. The method of claim 10, wherein one of said first face of said superstructure and said second face of said superstructure is at least partially coated with said non-solidified bone augmentation material.

18. The method of claim 10, wherein said superstructure further comprises at least one guide hole extending from said first face to said second face, said at least one guide hole sized and shaped to receive a tooth structure implant.

* * * * *